United States Patent [19]

Haber

[11] Patent Number: 5,064,434

[45] Date of Patent: Nov. 12, 1991

[54] GENITOURINARY IMPLANT

[76] Inventor: Terry M. Haber, 25011 Castlewood, El Toro, Calif. 92630

[21] Appl. No.: 647,680

[22] Filed: Jan. 28, 1991

Related U.S. Application Data

[63] Continuation of Ser. No. 504,761, Apr. 4, 1990, abandoned.

[51] Int. Cl.$^5$ .............................................. A61F 2/02
[52] U.S. Cl. .................................... 623/11; 606/198; 128/DIG. 25; 600/30
[58] Field of Search .......................... 623/1, 11, 12, 8; 606/191, 192, 194, 195, 198; 604/96, 104–109; 128/DIG. 25; 600/29, 30

[56] References Cited

U.S. PATENT DOCUMENTS

| | | |
|---|---|---|
| 1,271,456 | 7/1918 | Flack .................................... 606/198 |
| 3,568,659 | 3/1971 | Karnegis ............................. 604/105 |
| 4,552,128 | 11/1985 | Haber . |
| 4,686,962 | 8/1987 | Haber . |
| 4,773,393 | 9/1988 | Haber et al. . |
| 4,802,479 | 2/1989 | Haber et al. . |
| 4,832,680 | 5/1989 | Haber et al. ................ 128/DIG. 25 |

Primary Examiner—Randy Citrin Shay
Attorney, Agent, or Firm—Townsend and Townsend

[57] ABSTRACT

An apparatus for increasing local tissue volume at an injection site including an expandable containment membrane (4) for being hypodermically implanted into a patient. The containment membrane is implanted into the proximal periurethral tissue in an axially uninflated condition. An expansion mechanism (8) is permanently disposed within the containment membrane to add the desired bulk to the proximal periurethral tissues and thereby overcome urinary incontinence by locally controlling the increase of tissue volume. An actuation device (10) inflates the expansion mechanism, expanding the containment membrane in the radial direction. In one embodiment, the expansion mechanism is a plurality of axially elongated elements or spokes (14). Each spoke includes a distal end (16) and a proximal end (18), the ends being movable toward each other, causing the central portion of the spoke to move radially and thereby expand the containment membrane. In alternate embodiments, the containment membrane includes a plurality of nested containment membranes (4, 4',4"), sequentially inflated by injecting biocompatible fluid or suspended particulate matter. In each embodiment, the containment membrane functions as an envelope maintaining the expansion mechanism isolated from the surrounding tissue. The increased bulk of the expanded membrane increases passive occlusive pressure applied to the patient's urethra to control incontinence.

13 Claims, 12 Drawing Sheets

GENITOURINARY IMPLANT

This is a continuation of Ser. No. 07/504,761 filed Apr. 4, 1990, now abandoned.

BACKGROUND OF THE INVENTION

An artificial prosthesis sphincter may be implanted into a patient for applying occlusive pressure to the urethra and restore continence in cases where the natural sphincter muscles have been surgically excised or damaged by disease or physical trauma. Implantation of artificial sphincters commonly requires major surgery, necessitating hospitalization. The procedure is complex and usually takes six to eight weeks for recovery. In most cases, the patient also faces up to two additional months of delay before the success of the surgery can be ascertained, i.e., whether the patient is continent. Because of the swollen and aggravated condition of edema of the urethral tissues during and after surgery, the physician cannot precisely match the occlusive pressure of the patient's urethra. Therefore, he must estimate the minimal occlusive pressure required to achieve continence in the individual patient. This can result in improper selection and fitting of sphincteric devices. Therefore, occlusive pressures generated by these devices may be either insufficient to successfully achieve continence or excessive to the point of affecting blood flow and causing ischemia and subsequent erosion of the urethral tissue. Additional surgery may be required if the sphincter is insufficient to hold the patient continent or if it malfunctions. Further surgery may also be required for sphincter adjustment, repair or explant.

Urinary incontinence may be successfully treated by non-surgical means with periurethral injection of polytef paste to increase localized tissue volume. This increased localized tissue volume increases external occlusive pressure to the urethra, causing a partial obstruction and, thus, continence. However, substantial migration of polytef particles from the injection site often occurs. In addition, the paste may induce tissue reaction with Teflon ® granulomas. Thus, patient safety with use of the prior art devices is questionable, resulting in reduced application of this non-surgical procedure.

The assignee of the present invention is also assignee of U.S. Pat. No. 4,686,962 issued Aug. 18, 1987 entitled "Disposable Cartridge Assembly for Hypodermically Implanting a Genitourinary Prosthesis" and U.S. Pat. No. 4,832,680, issued May 23, 1989 entitled "Apparatus for Hypodermically Implanting a Genitourinary Prosthesis" the disclosures of which are hereby incorporated by reference. Briefly, the assemblies disclosed therein each include a non-surgical hypodermically implanted genitourinary prosthesis. A biocompatible fluid or suspended particulate material is injected into a single containment membrane to overcome urinary incontinence. Patient safety remains a primary concern, avoiding the toxic effects of Teflon ®-based paste and the migration of particles from the injection site.

SUMMARY OF THE INVENTION

The present invention provides a non-surgical hypodermically implanted genitourinary prosthesis. An elongated, expandable containment membrane is implanted into the patient in an axially uninflated condition. Urinary incontinence is overcome by adding the desired bulk to the proximal periurethral tissues. This is accomplished by radially expanding the containment membrane with an expansion mechanism inside the containment membrane for the controlled, localized increase of tissue volume. The expanded containment membrane increases the passive occlusive pressure applied to the patient's urethra, thereby controlling incontinence.

The membrane is inflated with the expansion mechanism while in situ so that no particle migration occurs since the containment membrane seals its interior against contact with the surrounding tissue. An actuator for the expansion mechanism remains coupled to the prosthesis while the membrane is inflated but is thereafter withdrawn, leaving the prosthesis in place where it applies the necessary pressure to the urethra to effect continence.

In a presently preferred form, the invention employs a plurality of axially oriented, flexible spokes, the ends of which are suitably held in axial alignment. The ends can be moved towards each other to thereby radially expand, or bulge the spokes outwardly and cause a corresponding, generally radially outward expansion of the enveloping membrane.

An elongated actuator expands the spokes radially outward and remains attached to the prosthesis during its insertion and subsequent volumetric expansion. The actuator takes the form of an elongated probe, the inner or distal end of which releasably engages the actuating mechanism of the prosthesis so that the necessary relative movements of the parts of the expansion mechanism can be safely effected without causing a separation of the actuator from the expansion mechanism and a possible premature "loss" of the inserted probe. Once the implantation procedure has been completed, i.e. once the necessary occlusive pressure has been applied to the urethra, the actuator is separated from the prosthesis, preferably the means of releasing a spring-biased connector between the two. The actuator is then withdrawn to complete the implantation procedure.

Another aspect of the present invention provides the prosthesis with a plurality of nested containment membranes. These are sequentially inflated by injecting biocompatible fluid or suspended particulate matter into them until the desired volumetric has been achieved to attain incontinence.

As generally described in U.S. Pat. No. 4,773,393 the containment membrane is implanted with a specialized dual hypodermic positioning, injecting and inflating instrument. It has a hollow outer trocar for dilating a suitably sized insertion channel through the targeted patient tissues. The containment membrane is axially movably disposed within the outer trocar in its folded or collapsed condition. A hollow stylus communicates with the interior of the containment membrane, extends through and projects from a proximate end of the trocar and places the membrane in communication with a source of biocompatible material for filling it. A needle at the end of the stylus is inserted into the interior region of the containment membrane through a self sealing valve core such that when the needle is removed, no biocompatible material can escape.

The interior region of each of the nested containment membranes is in communication with the interior region of the adjacent outer membrane by way a pressure sensitive valve which opens when the pressure inside the relatively inner membrane reaches a predetermined value. When this pressure has been reached the valve opens so that the inflation fluid can fill and thereby expand the next outer membrane. Thus, only one injection needle is required for inflating all of the containment membranes. Alternatively, a separate needle may of course be used to inject the inflation fluid into each containment membrane. The outermost containment membrane is always sealed to the environment.

Thus, the present invention provides a prosthesis for adding bulk to periurethral tissues to overcome urinary incontinence. The amount of inflation is readily and precisely controlled. The present invention therefore provides a safe, non-surgical procedure for controlling incontinence.

DETAILED DESCRIPTION OF THE PREFERRED EMBODIMENTS

Referring to FIGS. 1-28, an implantable prosthesis constructed in accordance with the present invention generally comprises a tubular, balloon like, elongated, expandable containment membrane 4 (sometimes also referred to as "balloon") for increasing local tissue volume at an injection site 6, as seen in FIGS. 8-14. The containment membrane is constructed of suitable tear-resistant, biocompatible, elastomeric material, such as silicon, polyurethane, latex or a like material. An expansion mechanism 8 is permanently disposed within the containment membrane for inflating it with an actuator 10 which is removed after implantation.

Referring particularly to FIGS. 1-7, prosthesis 2 has a central core pin 20 which is axially disposed inside containment membrane 4 and has a threaded aft or proximate end 32 and a semicircular head 26 at the opposite, remote or distal end. A tubular sleeve 22 is slipped over the threaded end of the pin and has a forward end fitted with a number, e.g. 8, axial grooves 46. Axial grooves 30 corresponding in number, orientation and position to the grooves 46 are formed in pin head 26. Elongated, flexible metal, e.g. stainless steel spokes 14 have their forward and aft ends 16, 18, retained within notches 30, 46, respectively.

Figures 1, 1A, 3, 4:
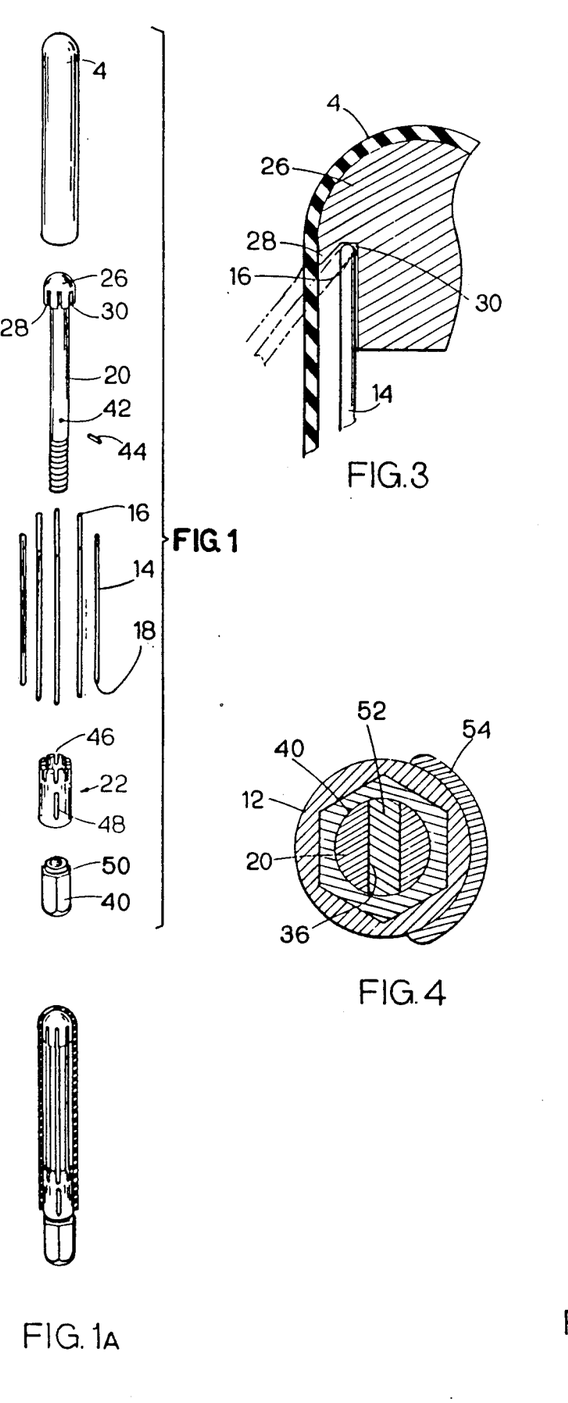
FIG. 1 is an exploded view of the genitourinary prosthesis of the present invention.
FIG. 1a is a sectional, perspective view of the prosthesis shown in FIG. 1.
FIG. 3 is a partial, enlarged, sectional view taken on line 3—3 of FIG. 2.
FIG. 4 is a cross-sectional view taken along line 4—4 of FIG. 2.
Figure 2:
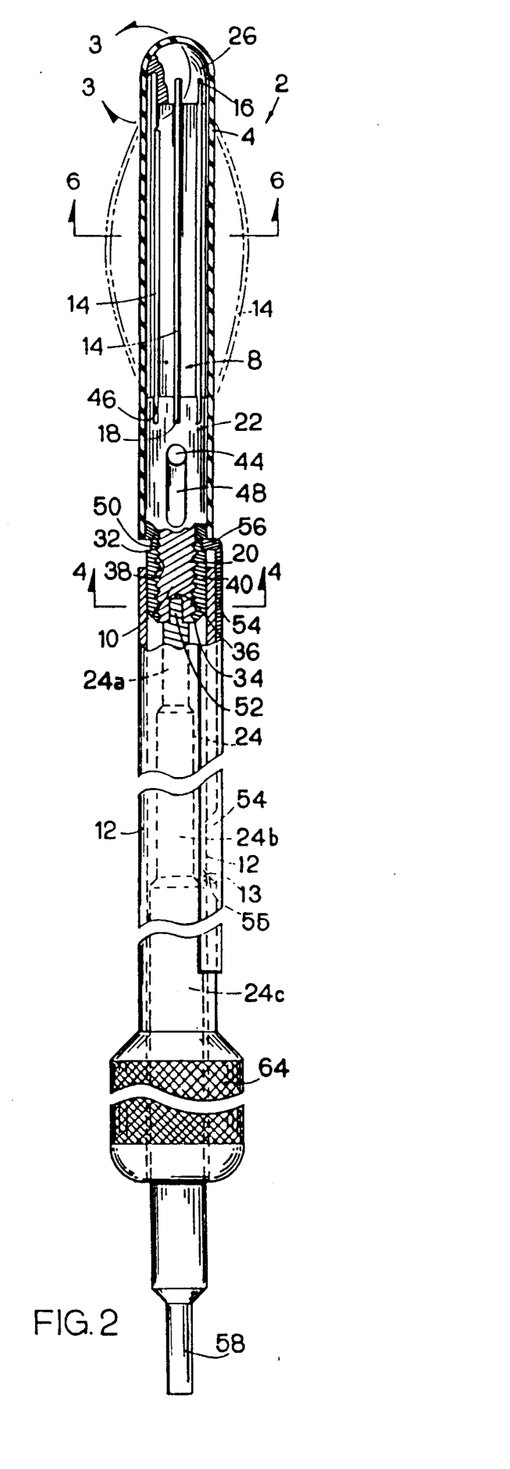
FIG. 2 is a cross-sectional view of the prosthesis of FIG. 1 showing its deflated state in solid lines and its expanded state in phantom lines.
Figure 5:
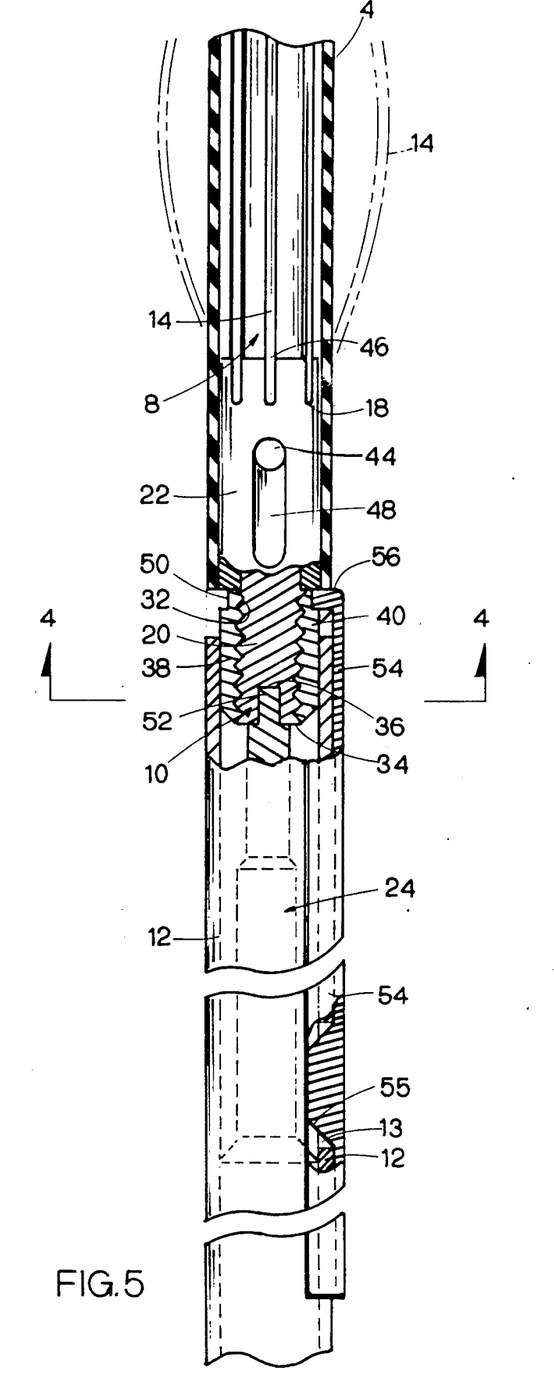
FIG. 5 is an enlarged view of the central portion of the prosthesis shown in FIG. 2.
Figure 6:
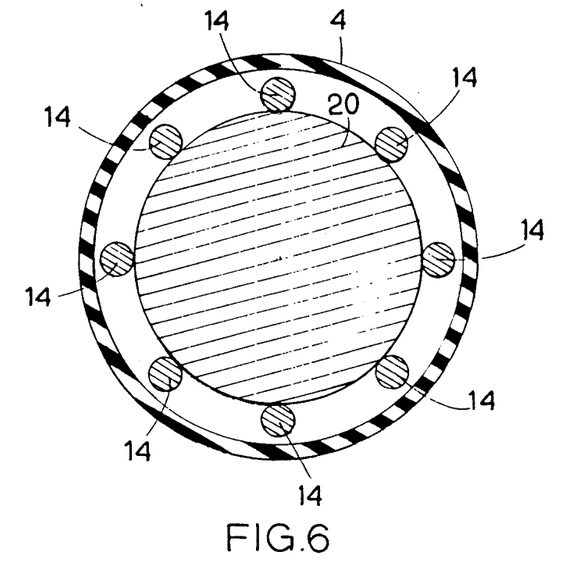
FIG. 6 is a section view through the uninflated containment membrane and is taken along line 6—6 of FIG. 2.
Figure 7:
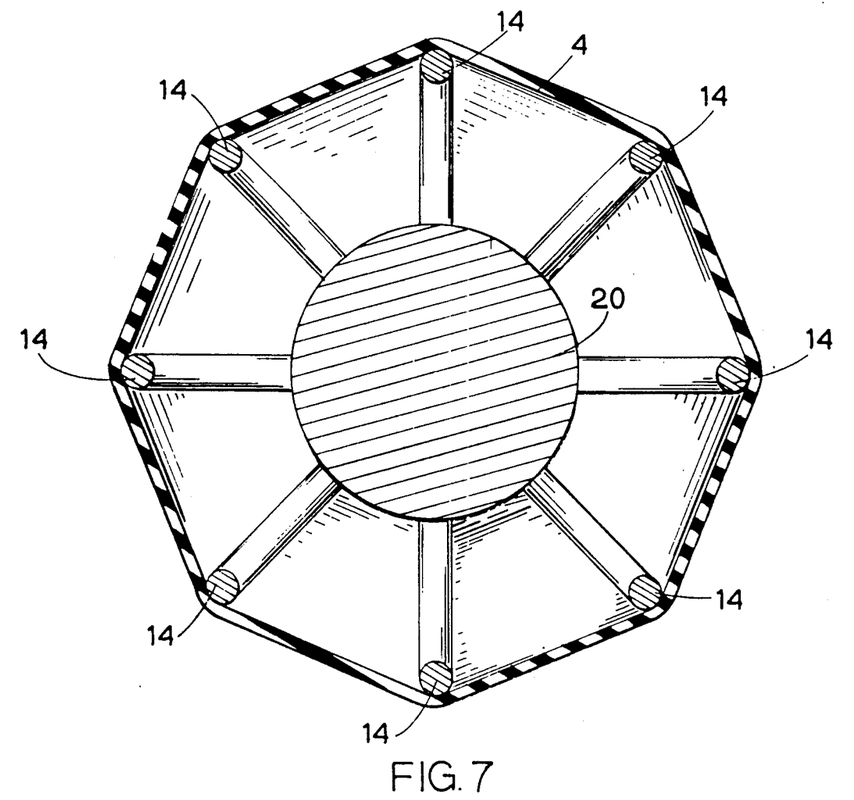
FIG. 7 is a view similar to FIG. 6 but shows the containment membrane in the expanded condition.
Figure 8:
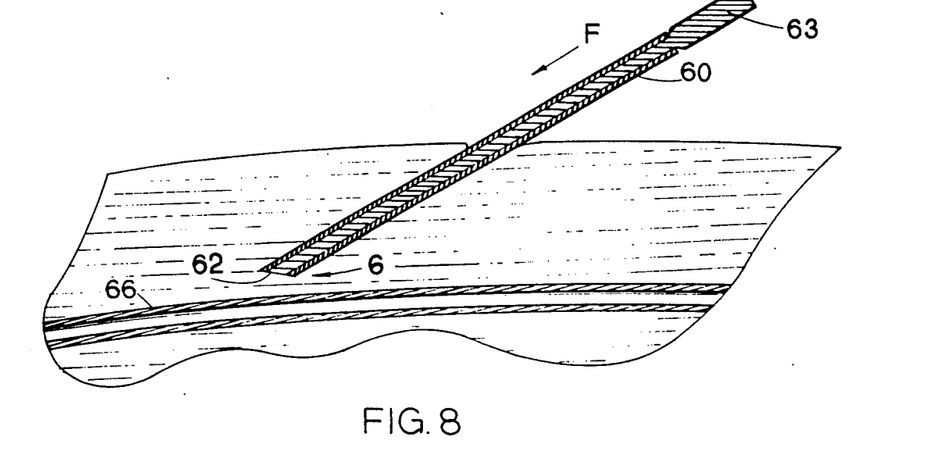
FIGS. 8-10 illustrate the insertion of the uninflated prosthesis into the tissue of a patient.
Figure 9:
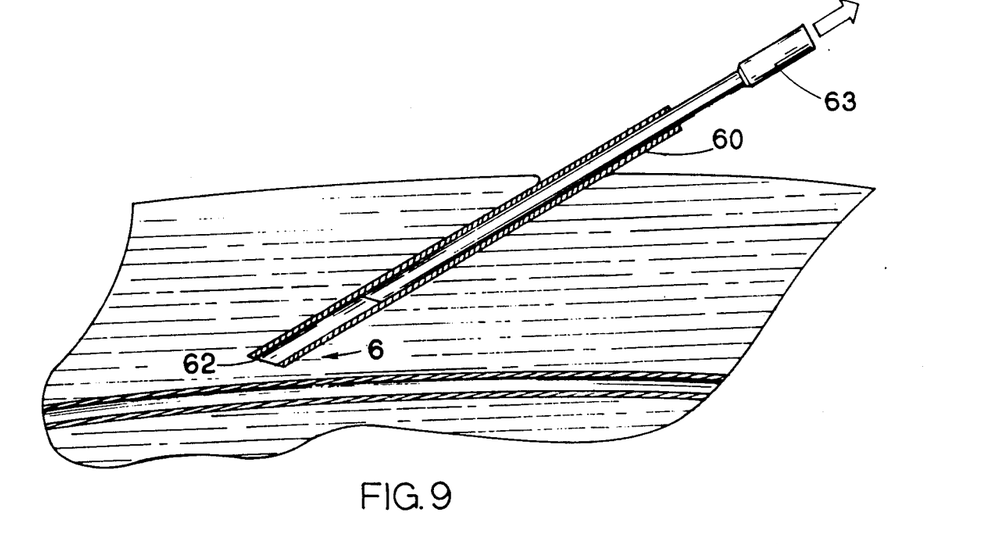

Pin 20, sleeve 22 and spokes 14 extend axially over the length of the containment membrane 4 which snugly engages all parts, biases them against each other and thereby retains them in their assembled form as is best seen in FIGS. 1A, 2 and 5. The open end of the membrane is sized to simply engage the exterior of the sleeve. The membrane may be bonded to the sleeve to prevent it from running axially along the sleeve, especially when the member is expanded.

The threaded end 32 of pin 20 projects past the aft end of the containment membrane. A hexagonal, somewhat elongated nut 40 is threaded onto end 32 and retains sleeve 22 on the pin. An axially oriented slot 48 in sleeve 22 is engaged by an arm 44 which projects radially from pin 20 and thereby prevents relative rotational motions between the pin and the sleeve. This maintains notches 30 and 46 and spokes 14 in axial alignment while permitting relative axial movements between the sleeve and the pin over the length of the slot. By turning nut 40, sleeve 22 can be moved axially in a forward direction from its fully retracted position (shown in FIG. 5), in which the spokes are parallel and closely adjacent to pin 20 (best shown in FIG. 6), to a more forward position. Such relative forward movement of the sleeve causes an outward bulging of spokes 14, as shown in phantom lines in FIG. 2, thereby correspondingly expanding the containment membrane in a generally radial direction into the position shown in FIG. 7 for correspondingly increasing the volume occupied by it.

To prevent a dislodging of the forward end 16 of spokes 14 from notches 30, during the assembly of the prosthesis, its storage or implantation, a radially outwardly and generally rearwardly extending lip 28 is formed by pin head 26 as is best illustrated in FIG. 3. The lip defines an overhang at the forward end of the notch into which the spoke is forcefully biased, especially during implantation and expansion of the containment membrane which assures a continued nesting of the spoke ends in the notches. A corresponding overhang and nesting end (not shown) can also be formed in notches 46 of sleeve 22 retaining the aft ends 18 of the spokes.

For purposes to be described later, an axially open, transverse slot 36 is formed in the aft end face 34 of threaded pin end 32. Further, the forward end of nut 40 which engages the rearwardly facing end of sleeve 22 has a radially open, circumferential retaining groove 50.

The actuator 10 for prosthesis 2 is best illustrated in FIGS. 2, 4 and 5. It includes an elongated tube 12, the forward end of which has an internal hexagonal shape to fit over and engage the exterior of nut 40. The aft end of the tube includes a knurled grip 64 of a preferably enlarged diameter. An elongated, flexible arm 54 has an aft end fixedly attached, e.g. spot-welded to the exterior of tube 12. The arm extends past the forward end of the tube and includes a radially inwardly oriented section 56 which is formed and positioned so that it engages groove 50 in nut 40 when the nut is inside the forward end of tube 12. A nose 55 projects radially inwardly from arm 54 at a point forward of the spot welds (or other means, not separately shown) which affix the arm to the exterior of the tube. It extends through an appropriately shaped and positioned aperture 13 in tube 12 into the interior thereof. By forcing the nose radially outwardly, in a manner further described below, arm 54 is forced outwardly as well, thereby disengaging the locking section 56 from groove 50 so that, thereafter, the tube 12 can be separated from the nut and the entire prosthesis 2 by axially moving them apart.

The actuator 10 further includes an elongated, cylindrical driver 24. Its forward end has a protrusion 52 which fits into slot 36 of core pin 20. The remainder of the driver is defined by three cylindrical sections 24a, b and c of increasing diameters (in an aft direction) with the diameter of the last section 24c being only slightly smaller than can be accommodated inside tube 12 to provide good guidance and support for the driver while permitting axial and rotational movements inside the tube. A second end 58 of the driver, shown protruding rearwardly from tube 12 in FIG. 2, has a reduced diameter and is joined to section 24c of the driver by a taper.

To disengage actuator 10 from the prosthesis, the driver is entirely removed from tube 12 and its second end 58 is inserted into it until the large diameter section 24c engages nose 55 of arm 54 and forces it in a radially outward direction. This moves arm section 56 out of groove 50 and enables the separation of the tube from the prosthesis.

Figure 10:
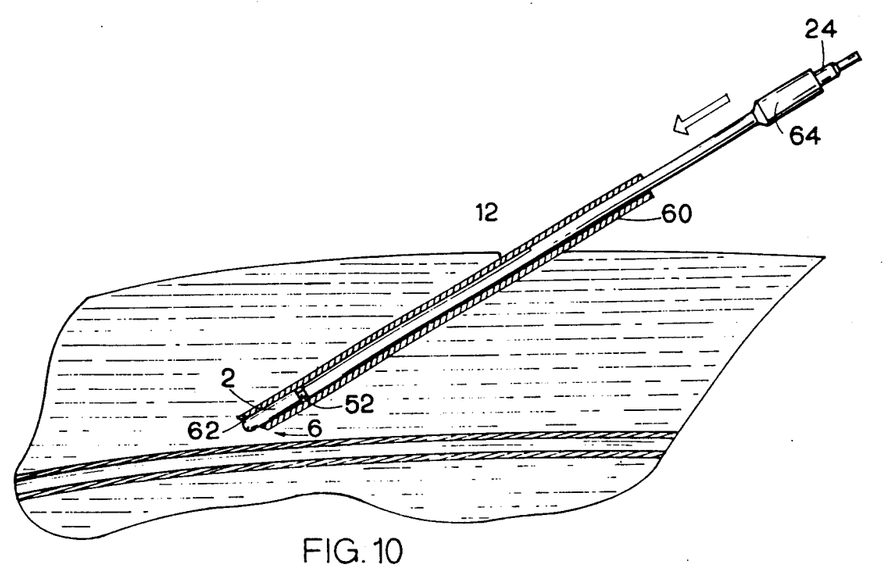
Figure 11:
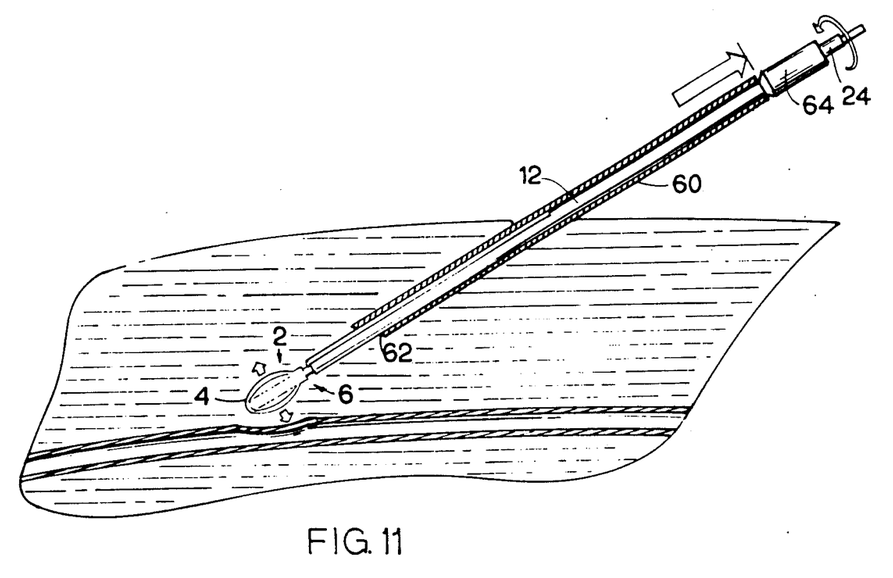
FIGS. 11-13 illustrate the in situ inflation of the containment membrane.
Figure 12:
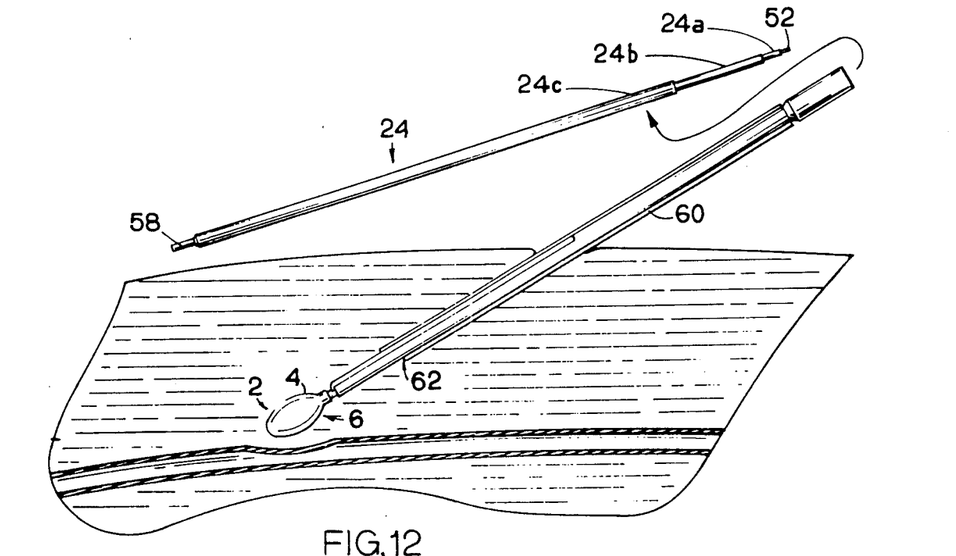
Figure 13:
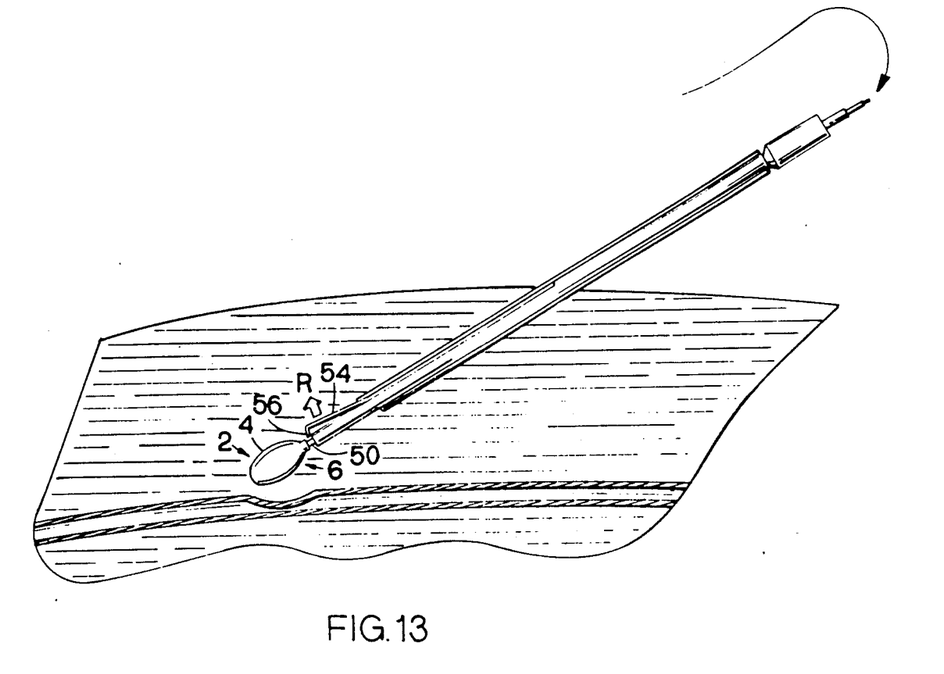

Turning now to the manner of implanting prosthesis 2 and referring to FIGS. 1-10, a tubular trocar 60 having a sharp cutting end 62 is appropriately placed against the patient's tissue and then advanced in a forward direction (in the direction of arrow F in FIG. 8) until the cutting edge is proximate to but spaced from urethra 66. A trocar plug 63, initially disposed within trocar 60, is withdrawn from the trocar and set aside. Next, and with trocar 16 in the illustrated position, a prosthesis 2, attached to actuator 10 by engaging nut groove 50 with radial arm section 56, is inserted into the trocar and axially advanced until the prosthesis is adjacent the cutting edge 62 of the trocar (illustrated in FIG. 10). Driver 24 is moved into tube 12 and its protrusion 52 is inserted into slot 36 of core pin 20. The trocar is now retracted (generally upwardly and to the right as seen in FIGS. 10-11) a sufficient distance to expose the prosthesis to the surrounding tissue. The knurled grip 64 and the outer end 58 of the driver are manually rotated relative to each other to move sleeve 22 in an axial direction toward pin head 26, thereby expanding the volume of the containment member 4 in the above-described manner. As schematically illustrated in FIG. 11, the increased volume of the containment membrane provides an occlusive pressure against the urethra 66. The expansion of the membrane by rotating driver 24 is continued until the physician has determined that the required pressure to stop incontinence has been applied.

Figure 14:
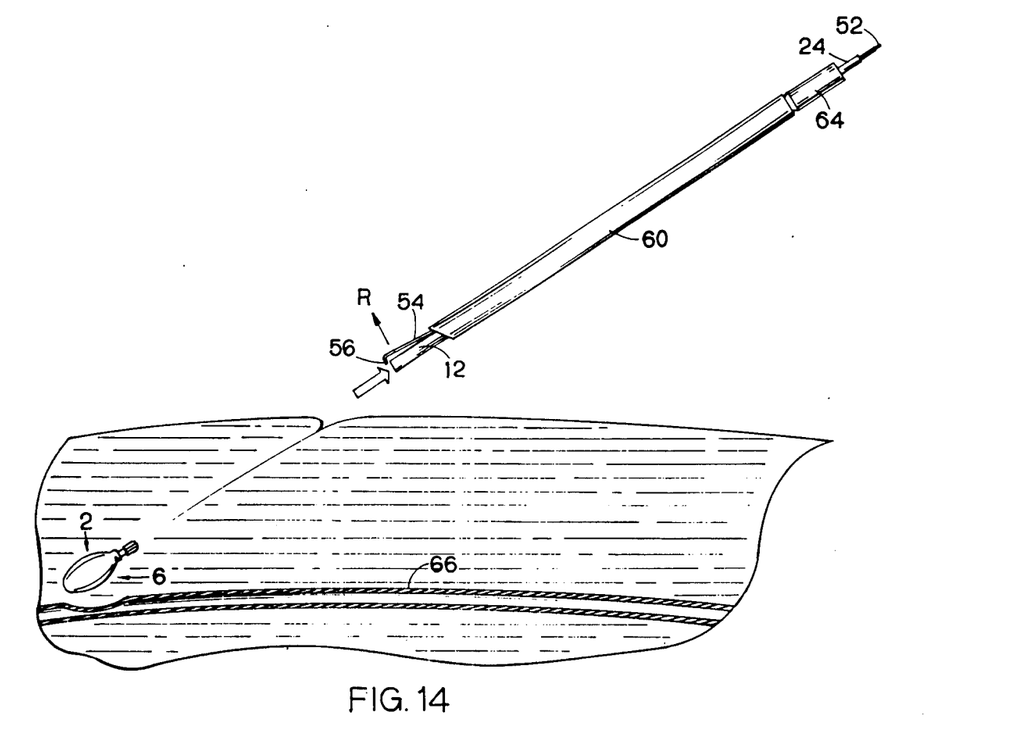
FIG. 14 illustrates the removal of the trocar from the patient.

Driver 24 is now retracted and reinserted into outer tube 12 with its second end 58 first. When the largest diameter section 24c of the driver arrives at aperture 13, nose 55 and therewith radial end section 56 of arm 54 is pushed radially outwardly to disengage the section from groove 50 in nut 40 as is sequentially illustrated in FIGS. 11-13. Trocar 60 with actuator 10 on its inside is now withdrawn, generally upwardly and to the right as shown in FIG. 14. Implant 12 remains in place and provides the desired pressure to compress urethra 66 sufficiently to assure continence.

Referring to FIGS. 15-22 an alternate inflatable prosthesis 102 has a plurality of nested containment membranes 4, 4' and 4". An expansion mechanism 8 is permanently disposed within the first, innermost containment membrane 4 for inflating the prosthesis actuator 10. Expansion mechanism 8 remains permanently within the containment membrane. The prosthesis is inflated and its volume is thereby increased by flowing a biometric fluid or suspended particulate matter through a needle 72 into the containment membrane 4, and, thereafter, sequentially into the others 4', 4". The injected material may include TEFLON ® particles or spheres, radio-opaque isotonic fluid, physiologic saline solution, or other matter.

Figure 15:
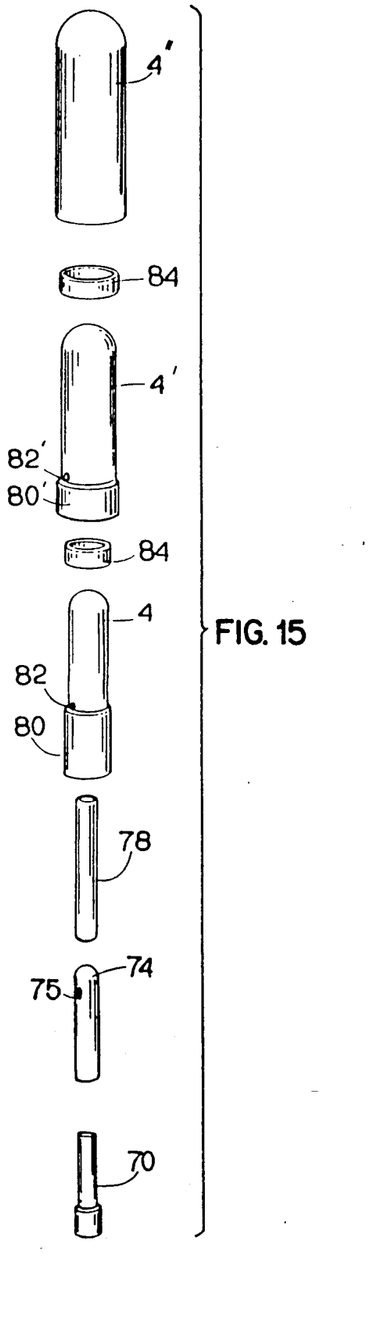
FIG. 15 is an exploded view of a prosthesis constructed according to an alternate embodiment of the invention.
Figure 16:
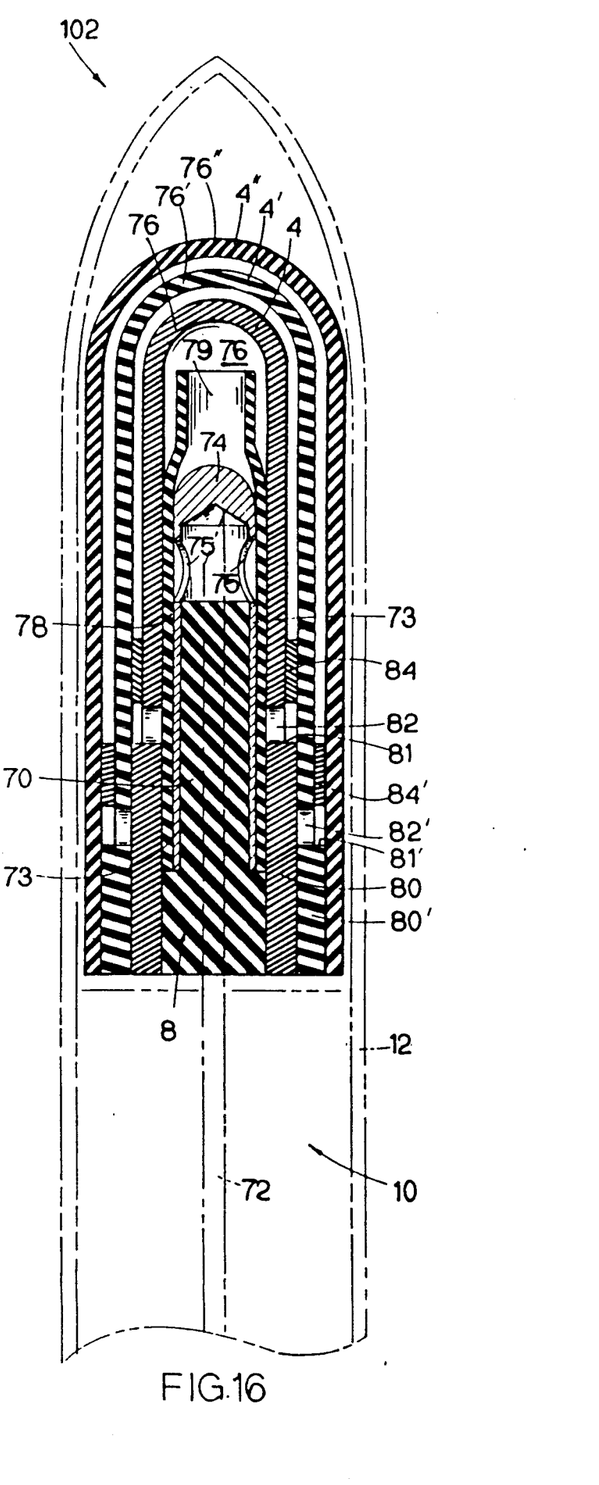
FIG. 16 illustrates the embodiment of FIG. 15 in its collapsed or unexpanded state inside the trocar.

Prosthesis 102 is hydraulically inflated, that is, it is inflated by injecting a fluid into the containment membranes. To this end, the prosthesis has a cylindrical core 70 constructed of a high memory, elastomeric polymer having a relatively low durometer so that, if the material is punctured by a needle and the needle is withdrawn, it self-seals the puncture and prevents leakage. A tubular sleeve 73 snugly fits over the core and extends past the forward end thereof. The sleeve ends in a head 74 which defines an interior needle stop surface 74a. The sleeve further includes a duality of apertures 75 positioned just forward of the core 70. The sleeve, including its head 74, are constructed of a suitable biocompatible, relatively rigid material such as stainless steel or relatively rigid plastic material, for example.

A flexible hose 78 constructed of a relatively soft, pliant and resilient, biocompatible material such as silicone, fits snugly over the outside of sleeve 73. Its open end 79 is in the interior 76 of the innermost containment membrane 4. The membrane has an elongated, cylindrical configuration, is closed at the far end and has an annular end section 80 of an enlarged thickness defining an annular shoulder 81. One or more openings 82 are formed in the first containment membrane immediately forward of shoulder 81 so that a fluid can flow from the interior of the containment membrane through the openings to the exterior thereof.

The second containment membrane 4' extends substantially concentrically over the first membrane 4 to contain the latter within the former. The second membrane also includes an enlarged diameter end section 80' which snugly encircles and fits over the end section 80 of the inner membrane. A shoulder 81' is formed by the end section of the second membrane and the latter includes one or more openings 80" positioned just forward of the shoulder and overlying the enlarged diameter end section 80 of the innermost membrane 4.

In addition, a tubular sealing band 84 constructed of a relatively soft, resilient material such as silicone, is disposed between the innermost and the intermediate membranes 4, 4'. The containment membranes are dimensioned so that in their relaxed states, they retract sufficiently to press sealing band 84 against both membranes, thereby preventing the flow of fluid through aperture 82 and past the band until a predetermined threshold pressure level has been reached in a manner and for purposes more fully described below.

Lastly, an outermost containment membrane 4" envelopes the other membranes. Its aft portion snugly grips the enlarged end section 80' of the intermediate membrane and thereby establishes a seal between them so that no fluid can flow past it. Another tubular sealing band 84' is disposed in the space between the intermediate and outer containment membranes 4', 4" just forward of apertures 82' in the intermediate membrane. This tubular sealing band is also "squeezed" between the intermediate and outermost membranes to form a seal up to a predetermined threshold pressure between the interior spaces 76' and 76" of the intermediate and outermost membranes.

Figure 18:
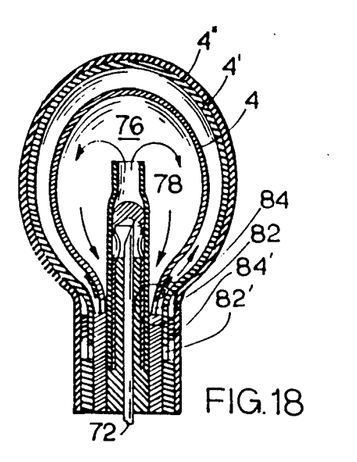
Figure 19:
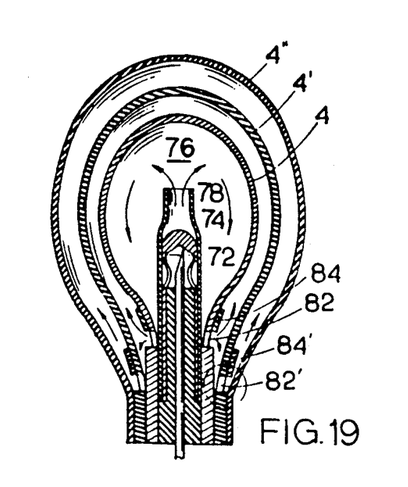
Figure 20:
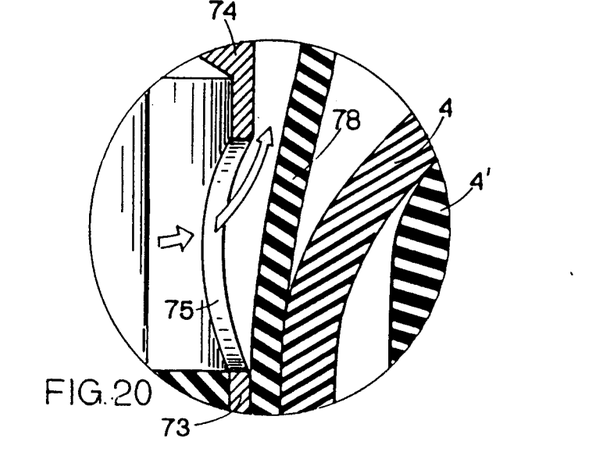
Figure 21:
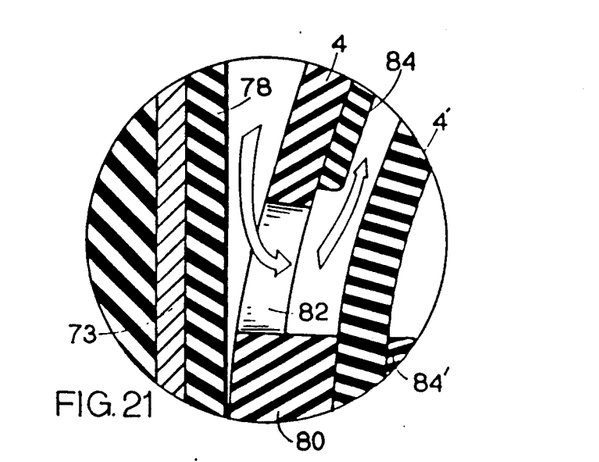
Figure 22:
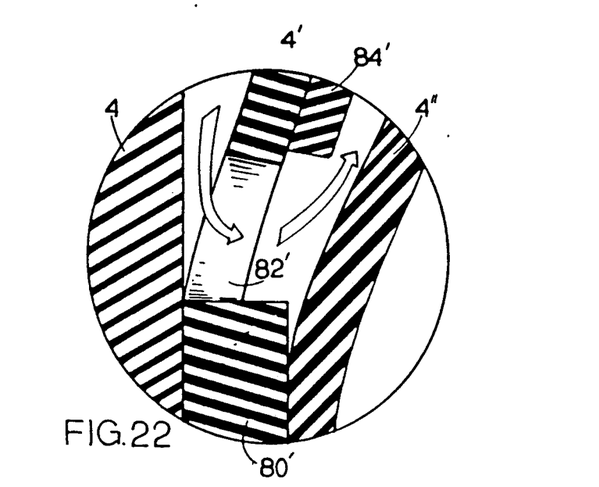

Referring now especially to FIGS. 17-22, the prosthesis 102 shown in FIGS. 15 and 16 is inflated by extending a needle 72 through the self-sealing valve core member 70 until the needle end engages and its further forward travel is prevented by needle stop surface 74a. A suitable inflation fluid is now flowed through the needle and past apertures 75, open hose end 79 into the interior 76 of innermost membrane 4, thereby expanding it and giving it the bulbous shape shown in FIG. 17. FIG. 20 shows the direction of flow of fluid discharged from the needle past aperture 75, the expansion of the resilient hose 78 under the fluid pressure in a radial direction to enable fluid flow from the aperture to the open end 79 of the hose, and the radial expansion of the innermost membrane.

Figure 17:
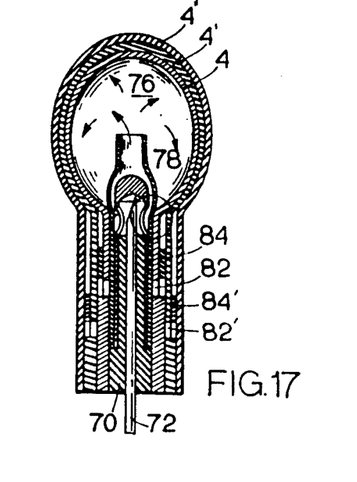
FIGS. 17-22 illustrate the sequential inflation of nested containment membranes.

As fluid continues to flow from the needle into the interior 76 of the first membrane, its continued expansion is accompanied by a corresponding increase in the prevailing fluid pressure. As the innermost membrane expands volumetrically under the increasing pressure it peels away from hose 78 and fluid eventually flows through aperture 82 and against the tubular sealing band 84 between the inner and intermediate membranes 4, 4'. This lifts the intermediate membrane 4' off band 84 so that fluid eventually flows through aperture 82 into the interior space 76' of the intermediate aperture.

From this point on, the continued injection of fluid from needle 72 causes a radial expansion of the intermediate membrane into the position illustrated in FIG. 18.

Continuing fluid flow through needle 72 eventually establishes fluid communication between the interior space 76' and aperture 82' in the intermediate membrane 4' (see FIG. 22) and, thereafter, lifts the outermost membrane off the tubular sealing band 84'. Thus, the discharge of pressurized fluid from the needle eventually leads to the expansion of the outermost membrane 4" as is best seen in FIG. 19.

The implantation procedure for prosthesis 102 follows those described above with reference to FIGS. 8-14 as far as the appropriate positioning of the prosthesis in the proximity of the patient's urethra is concerned. However, instead of mechanically operating the expansion mechanism 8 of the prosthesis, it is hydraulically activated by extending a needle through the trocar and penetrating the self-closing core 70 of the prosthesis before the latter is inserted in the trocar. The needle can then be used to axially advance the prosthesis through the trocar to the desired implantation location. Once there, the trocar is slightly retracted to expose the prosthesis to the surrounding tissue. Fluid is then flowed through the needle into the innermost containment membrane and, thereafter, sequentially into the outer ones until the desired volumetric expansion to effect continence has been attained. At that point, the needle is withdrawn from the prosthesis into the interior of the trocar. The self-sealing core 70 prevents the escape of any of the just-injected fluid from the interior of the containment membranes to the exterior thereof.

Figures 23, 24:
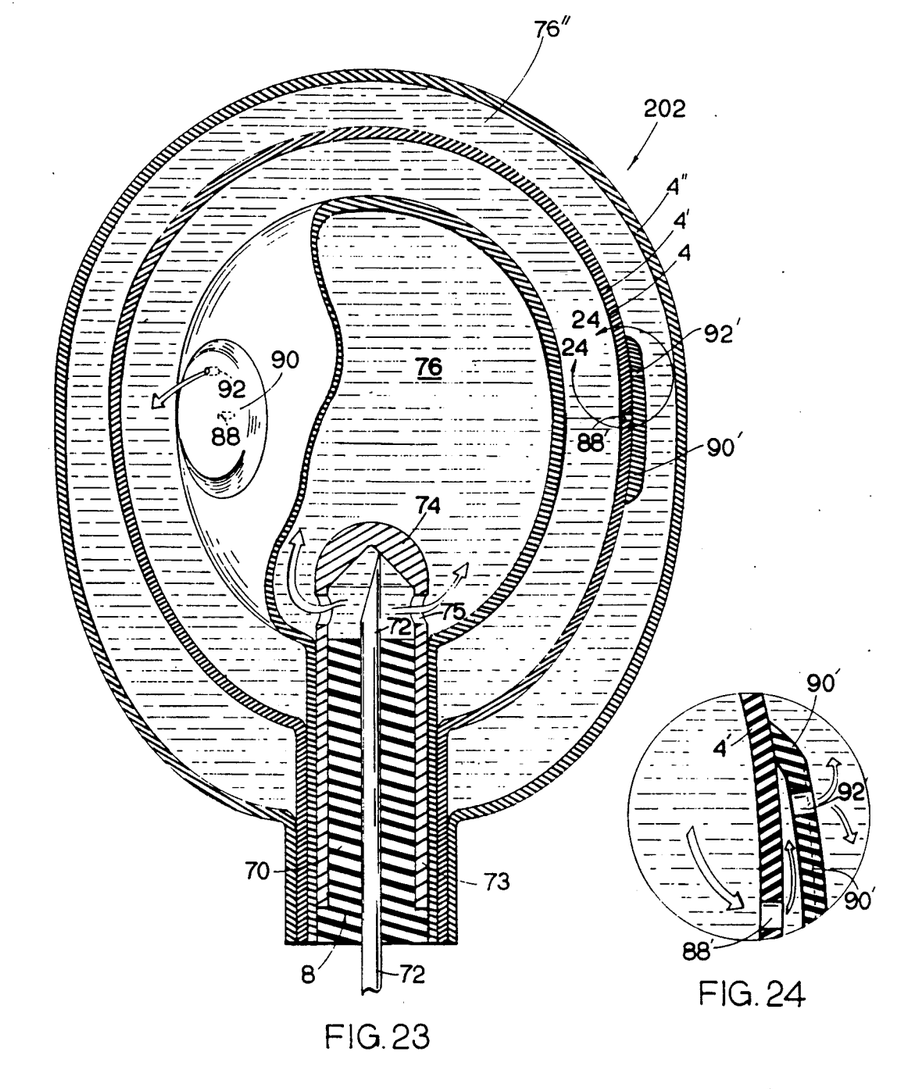
FIG. 23 illustrates a prosthesis constructed according to a third embodiment of the present invention.
FIG. 24 is an enlarged, fragmentary view in section and is taken along line 24—24 of FIG. 23.
Figure 25:
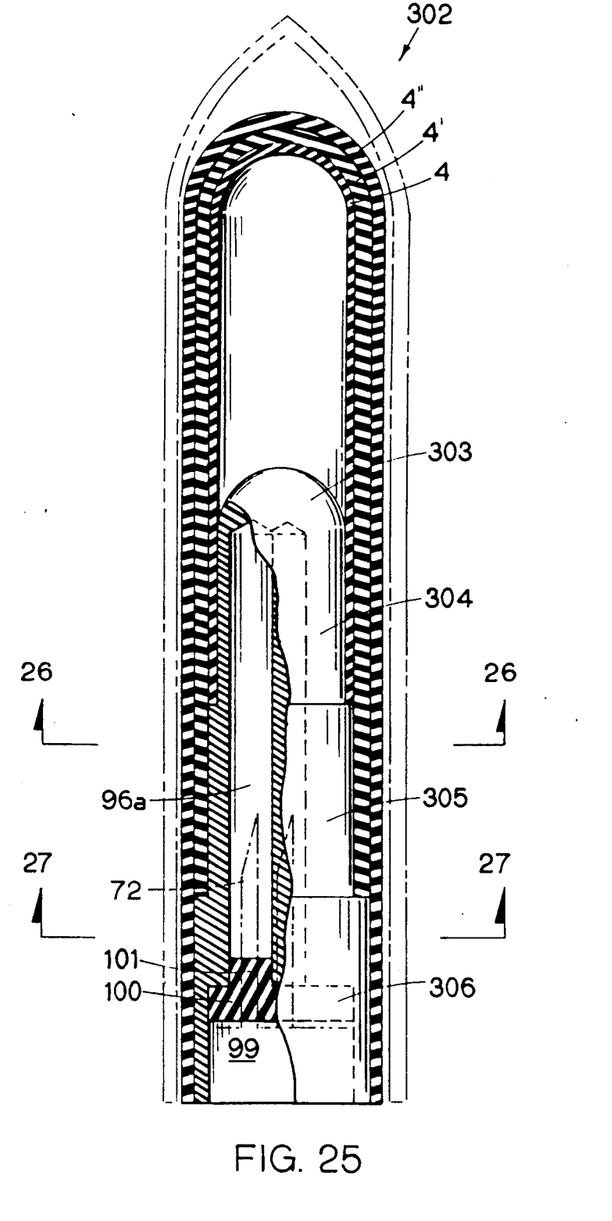
FIG. 25 illustrates a further embodiment of the prosthesis having multiple, nested containment membranes.
Figure 26:
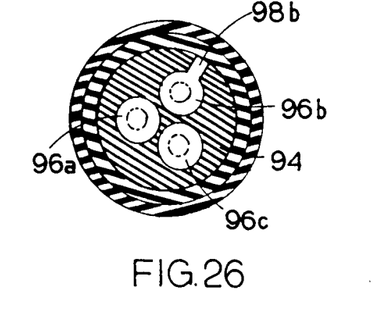
FIGS. 26 and 27 are cross-sectional views taken along lines 26—26 and 27—27 of FIG. 25, respectively.
Figure 27:
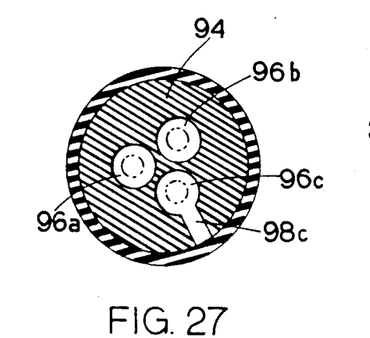

Referring now to FIGS. 23 and 24, in another embodiment of the present invention a prosthesis 202 is again constructed of a plurality, e.g., three nested containment membranes 4, 4', 4". As with the embodiment illustrated in FIGS. 15 and 16, the prosthesis includes a cylindrical core 70 constructed of a self-sealing elastomeric material and defining part of the expansion mechanism 8. The elongated sleeve 73 tightly engages the exterior of the core, extends past the forward end thereof and forms a head 74 including a needle stop surface 74a. The containment membranes, in their relaxed state (not shown) firmly grip the aft end of the core and the sleeve, establish seals between them, and they extend axially in a forward direction past head 74.

Sleeve 73 includes one or more apertures 75 which lead to the interior 76 of the innermost containment membrane 4. In addition, the inner and intermediate membranes each include one or more fluid flow opening(s) 88, 88' which are sealed by elastomeric disk membranes 90, 90' of a substantially larger diameter than the openings. The periphery of each disk is affixed, e.g., bonded to the exterior of the associated membrane. Each disk further includes a valve opening 92, 92' which is spaced from both the associated membrane 88, 88' and the bonded periphery of the disk so that, when pressurized fluid is within the membrane it eventually lifts the disk off the membrane and thereby fluidly communicates openings 88, 92 (and 88', 92') when a predetermined threshold pressure is reached as is best illustrated in FIG. 24.

In use, and after the prosthesis 202 has been properly positioned in the patient's tissue, fluid is injected through needle 72 into the interior 76 of the first membrane. It expands until the pressure therein reaches a level at which the sealing disk 90 is lifted and fluid can flow through openings 88 and 92 into the interior space 76' of the intermediate membrane 4'. If further expansion is desired, the same process is continued until fluid flows through openings 88', 92', into the interior 76" of the outermost membrane as is illustrated in FIG. 23.

Figure 28:
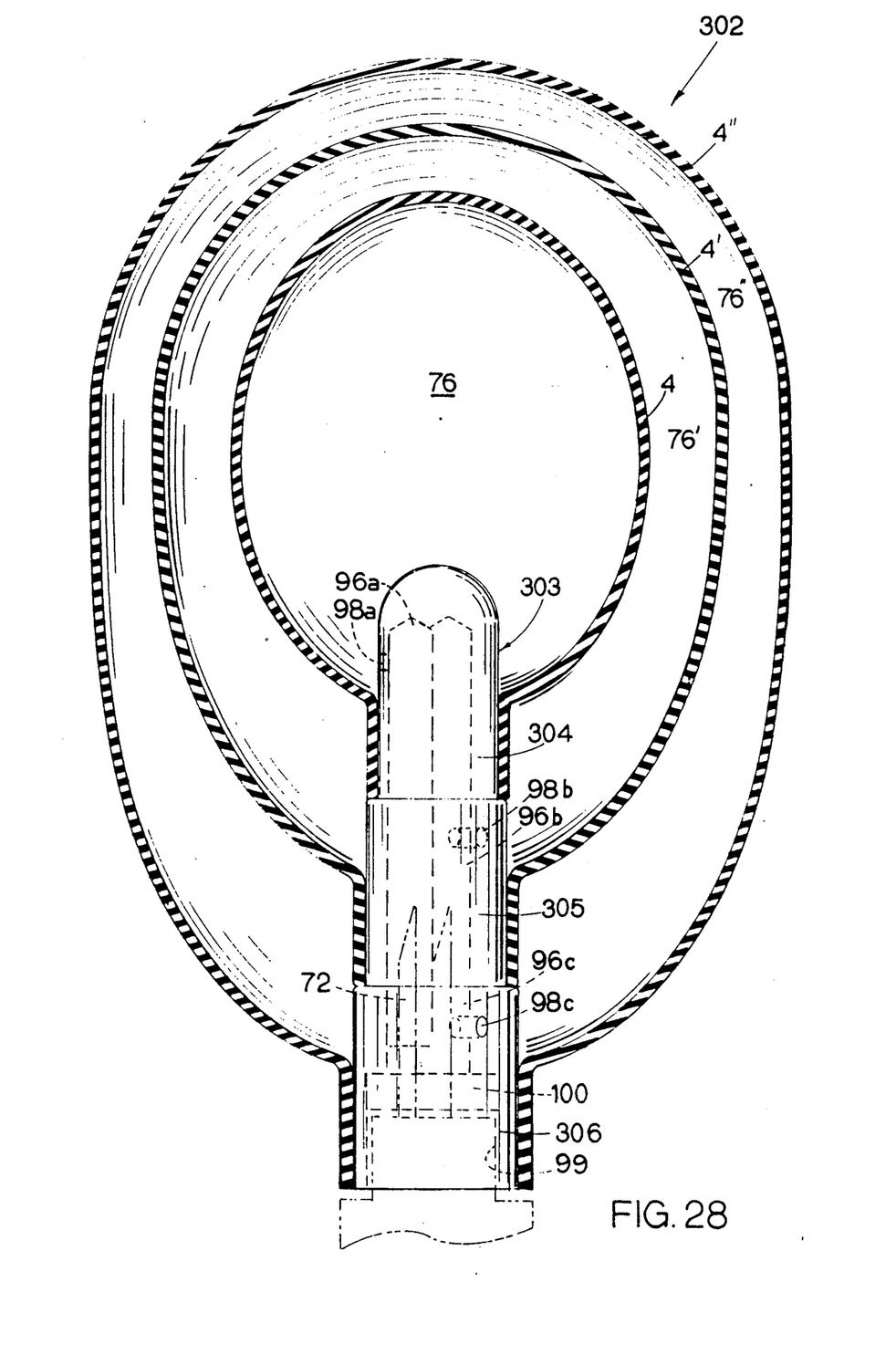
FIG. 28 illustrates the embodiment of FIG. 25 in its partially expanded state.

Referring now to FIGS. 25-28, in a still further embodiment of the present invention, a prosthesis 302 is again defined by three nested expansion membranes 4, 4' and 4" which fit over a generally cylindrical core 303 defined by an inner core section 304, an intermediate section 305 and an upper core section 306, each of slightly larger diameter than the preceding one. The inner to outermost containment membranes snugly and sealingly engage the inner to outermost core sections as is best illustrated in FIG. 28. The principal difference between prosthesis 302 and the one shown in FIGS. 23 and 24 is that there is no fluid communication between the interiors 76, 76' and 76" of the membranes. Instead, core 303 includes three spaced-apart, axially extending bores 96a, b and c which communicate via radial openings 98a, b and c, with the membrane interiors 76, 76' and 76", respectively.

The aft end of core 303 has a cylindrical recess 99. A self-sealing, elastomeric plug 100 is nested in the recess and can be provided with extensions 101 into the axial apertures 96a-c to seal each aperture after the withdrawal of the needle 72 subsequent to the implantation and full expansion of the prosthesis.

The prosthesis 302 shown in FIGS. 25-28 is implanted in the same manner in which prosthesis 202 shown in FIGS. 23 and 24 except that three needles 72 are extended through the trocar (not shown in FIGS. 25-28) and into the appropriate bores 96a-c in core 303.

What is claimed is:

1. An implant for volumetrically increasing the volume of a body portion comprising:
   an elastomerically expandable, elongated, generally tubular membrane having an open end;
   expansion means disposed within the membrane including a plurality of elongated members extending over a portion of the length of the membrane and means for moving the elongated members radially outward to thereby correspondingly radially expand the membrane;
   actuator means operatively coupled with the expansion means for activating the moving means from an exterior of the body tissue while the membrane and the expansion means is surrounded by body tissue; and
   release means for permitting the separation of the actuator means from the expansion means after the desired radial expansion of the membrane has been achieved.

2. An implant according to claim 1 wherein the elongated members comprise a plurality of elongated spokes extending substantially parallel to the length of the membrane and circumferentially spaced about an interior thereof.

3. A prosthetic implant according to claim 2 wherein the expansion means further comprises:
   an axially extending core pin having a first end on an interior of the membrane and a second end at the open end of the membrane, the pin being disposed radially inward of the spokes and having means at the first end retaining proximate ends of the spokes;
   an axially movable, nonrotatable sleeve on the second end of the pin including means for retaining the other ends of the spokes;
   means preventing relative rotational movements between the sleeve and the core pin; and
   wherein the moving means comprises means for axially moving the sleeve towards the first end of the core pin to thereby bulge the spokes intermediate their ends radially outwardly and effect a corresponding radial outward expansion of the membrane.

4. An implant according to claim 3 wherein the means for axially moving the sleeve comprises a nut threadably engaging the second end of the core pin and engaging an end of the sleeve so that rotation of the nut causes axial movement of the sleeve along the pin.

5. A prosthetic implant according to claim 1 wherein the expansion means includes a core member axially disposed within the membrane, disposed radially inward of the elongated members, and supporting the ends of the members in their axial alignment, a nut threadably engaging the core member at an end thereof proximate the open end of the membrane, and means operatively coupling the nut with proximate ends of the elongated members so that relative rotation of the nut on the core number causes a corresponding axial movement of the ends of the members relatively to each other, thereby bulging the members radially outwardly to effect the radial outward expansion of the membrane surrounding the members.

6. An implant according to claim 5 wherein the actuator means comprises a tube means having a first end non-rotationally engaging an exterior of the nut and a length sufficient so that another end thereof protrudes from the tissue during an implantation procedure; and wherein the release means includes means for releasably connecting the tube means to the nut.

7. An implant according to claim 6 wherein the means for connecting comprises a radially open groove formed in the nut proximate an end thereof facing an interior of the membrane;
   spring arm means mounted to an exterior of the tube means and having an end extending beyond an end of the tube means and biased into the open groove in the nut; and
   wherein the release means includes means for disengaging the spring arm means from the groove in the nut after completion of the implantation procedure to permit the separation of the actuator means from the expansion means by moving the tube means in an axial direction away from the nut.

8. An implant according to claim 7 wherein the release means comprises a radially inwardly oriented projection on the spring arm means extending into an interior of the tube means, and driver means axially movable within the tube means for engaging the projection and moving it radially outward to thereby disengage the spring arm means from the groove in the nut.

9. An implant according to claim 8 wherein the driver means is rotationally movable within the tube means, and including means on the driver means and the core number for non-rotationally, detachably connecting them so that relative rotational movements between the driver means and tube means while the spring arm means engages the nut groove causes a corresponding relative rotational movement between the nut and the core member to thereby expand the elongated members radially outwardly.

10. An implant for locally increasing the volume of tissue to control the flow of body fluids through a body fluid passage comprising:
    an elongated, generally tubular, resilient and flexible membrane having a closed end and an open end;
    a mechanical expansion mechanism disposed within the membrane including an elongated core pin extending over about the length of the membrane and having an inner head proximate the closed end of the membrane and a threaded end protruding from the open end of the membrane, a plurality of elongated, axially oriented, resiliently flexible spokes disposed about the pin, an axially movable sleeve non-rotatably carried by the pin adjacent the threaded end thereof, the head and the sleeve including cooperating notches for retaining the spokes in their axial orientation and relative positions; and
    a nut on the threaded end of the pin and engaging the sleeve so that rotation of the nut causes a corresponding axial movements of the sleeve along the pin; and
    the membrane being constructed to snugly and resiliently engage the mechanical expansion mechanism and maintain them in their preassembled arrangement;
    whereby rotation of the nut causes the spokes to bulge radially outwardly to effect a corresponding radial outward expansion of the membrane.

11. An implant according to claim 10 including means securing the open end of the membrane to the sleeve to prevent substantial axial movements between the open end of the membrane and the sleeve when the nut is rotated.

12. An implant according to claim 11 including means for positioning the implant within the tissue and rotating the nut relative to the pin from the exterior while the implant is in place comprising an elongated tube having a first end axially movable relative to and non-rotatably engaging the nut and a second, exterior end, driving means rotatably and axially movable within the tube having a first end releasably and non-rotatably engageable with the pin and a second end projecting from the tube; whereby relative rotation between the tube and the driving means causes corresponding relative rotation between the nut and the pin and thereby the desired outward bulging of the spokes; and means for releasably securing the tube to the nut and thereby to the implant.

13. An implant according to claim 12 wherein the means for releasably securing comprises a retaining arm carried by the tube adjacent its first end and biased into engagement with the nut to prevent relative axial motions between them; and means activatable with the driving means from the interior of the tube for disengaging the retaining arm from the nut to permit them to be axially moved apart and separated after completion of the implantation process.

* * * * *